United States Patent
Gonzalez

(10) Patent No.: US 11,554,046 B2
(45) Date of Patent: Jan. 17, 2023

(54) IRIS REGISTRATION METHOD FOR OPHTHALMIC LASER SURGICAL PROCEDURES

(71) Applicant: AMO Development, LLC, Irvine, CA (US)

(72) Inventor: Javier Gonzalez, Palo Alto, CA (US)

(73) Assignee: AMO Development, LLC, Irvine, CA (US)

(*) Notice: Subject to any disclaimer, the term of this patent is extended or adjusted under 35 U.S.C. 154(b) by 0 days.

(21) Appl. No.: 17/057,102

(22) PCT Filed: Oct. 28, 2019

(86) PCT No.: PCT/IB2019/059231
§ 371 (c)(1),
(2) Date: Nov. 20, 2020

(87) PCT Pub. No.: WO2020/089774
PCT Pub. Date: May 7, 2020

(65) Prior Publication Data
US 2021/0244565 A1  Aug. 12, 2021

Related U.S. Application Data

(60) Provisional application No. 62/755,122, filed on Nov. 2, 2018.

(51) Int. Cl.
*A61F 9/008* (2006.01)
*G16H 30/40* (2018.01)
*G06T 3/40* (2006.01)

(52) U.S. Cl.
CPC ............ *A61F 9/008* (2013.01); *G06T 3/4084* (2013.01); *G16H 30/40* (2018.01); *A61F 2009/00876* (2013.01)

(58) Field of Classification Search
CPC ............ A61F 9/008; A61F 2009/00876; A61F 9/00834; A61F 2009/00855;
(Continued)

(56) References Cited

U.S. PATENT DOCUMENTS

2011/0224657 A1   9/2011   Stevens et al.
2015/0018674 A1*  1/2015   Scott ............... A61B 5/0073
                                            600/407

(Continued)

FOREIGN PATENT DOCUMENTS

WO    03102498 A1   12/2003
WO    2009135084 A1  11/2009
WO    2011035063 A1   3/2011

OTHER PUBLICATIONS

International Search Report and written opinion for Application No. PCT/IB2019/059231, dated Jan. 30, 2020, 6 pages.

*Primary Examiner* — Gary Jackson
*Assistant Examiner* — Sebastian X Lukjan
(74) *Attorney, Agent, or Firm* — Johnson & Johnson Surgical Vision, Inc.

(57) ABSTRACT

In a laser cataract procedure that also corrects for astigmatism, an iris registration method compares an iris image of a patient's eye taken when the eye is not docked to a patient interface device with an iris image of the same eye that is docked to the patient interface, to calculate a rotation angle between the two images. The astigmatism axis of the eye is measured when the eye is not docked, and the measured axis is rotated by the calculated rotation angle to obtain a rotated astigmatism axis relative to the iris image of the docked eye. The laser cataract procedure is performed based on the rotated astigmatism axis. The rotation angle is calculated by optimizing a transformation that transforms the undocked iris image to match the docked iris image, where the
(Continued)

transformation includes a dilation factor that accounts for different pupil dilation of the two iris images.

20 Claims, 6 Drawing Sheets

(58) Field of Classification Search
CPC .... A61F 2009/0087; A61F 2009/00872; A61F 9/00827; A61F 9/009; A61F 2009/00846; A61F 2009/00897; G06T 3/4084; G16H 30/40; G16H 20/40; A61B 18/20; A61B 3/0025; A61B 3/1035; A61B 3/145
See application file for complete search history.

(56) References Cited

U.S. PATENT DOCUMENTS

| | | |
|---|---|---|
| 2017/0056243 A1 | 3/2017 | Georg et al. |
| 2017/0151089 A1 | 6/2017 | Chernyak |
| 2018/0125355 A1* | 5/2018 | Mrochen .............. A61B 3/0025 |

* cited by examiner

12

IRIS REGISTRATION METHOD FOR OPHTHALMIC LASER SURGICAL PROCEDURES

CROSS REFERENCE TO RELATED APPLICATIONS

This application is a U.S. national stage of and claims the benefit under 35 U.S.C. § 371 of International Patent Application No. PCT/IB2019/059231, filed Oct. 28, 2019, which claims the benefit under 35 U.S.C. § 119(e) of U.S. Provisional Patent Application No. 62/755,122 filed Nov. 2, 2018, which are incorporated herein by reference in their entirety.

BACKGROUND OF THE INVENTION

Field of the Invention

This invention relates to an iris registration method for an ophthalmic laser surgical procedure, and in particular, it relates to an iris registration method for registering corneal astigmatism measurement results to docked eye images.

Description of Related Art

Ultrashort (e.g. femtosecond) pulsed laser systems are used to perform laser cataract procedures, which includes using the laser beam to make incisions on the surface of the eye such as the cornea or sclera, make incisions on the lens capsule, and fragment the lens for easy removal. After the lens is removed, an intraocular lens (IOL) is implanted in the lens capsule. The same laser system may be used to correct corneal astigmatism while performing the cataract procedure, for example, by making arcuate relaxation incisions in the cornea or sclera to change the tension in the cornea, and/or by using a toric IOL and accurately aligning the IOL relative to the axis of corneal astigmatism, provided that the patient's corneal astigmatism (the a-sphericity, including the orientation of the steep meridian) is known. A patient's corneal astigmatism may be measured beforehand using the imaging capabilities of the laser system used to perform the cataract procedure, or on a diagnostic device that is separate from the laser system. When measuring the astigmatism, the patient's eye is free of any mechanical contact with the laser system or the diagnostic device, i.e., the eye is not mechanically coupled to the patient interface (PI) device that is typically used during laser cataract procedures. This is because the cornea is easily deformable and its sphericity will change temporarily when the eye is coupled to the PI device, preventing an accurate astigmatism measurement.

After the astigmatism is measured, the patient's eye is mechanically coupled to the patient interface device of the laser system (referred to as docking of the eye) in order to carry out the cataract procedure. Thus, the actual orientation of corneal astigmatism of the docked eye (the eye that is coupled to the PI) may be different from the previously measured orientation because of possible cyclorotation and docking-induced rotation of the eye.

Conventional means of registering the patient's axis of astigmatism (e.g. the steep meridian of the cornea) to the coordinate frame of the laser system include visually evaluating the eye using a video image of the eye taken by an onboard imaging system and manually placing ink marks on the eye. In another conventional method, the physician manually aligns fiducial features of the patient interface device to the patient's eye. Sometimes the possible rotations of the eye are simply ignored, and the axis of astigmatism is aligned to the laser system's coordinate frame without compensation for cyclorotation and docking-induced rotation of the eye.

SUMMARY

Accordingly, the present invention is directed to an iris registration method and related apparatus that substantially obviates one or more of the problems due to limitations and disadvantages of the related art.

An object of the present invention is to accurately determine the orientation of astigmatism of an eye that is docked to the laser system.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a laser ophthalmic surgery system for treating a patient's eye, which includes: a laser source configured to generate a pulsed laser beam; an optical delivery system coupled to the laser source, and configured to receive and direct the pulsed laser beam; a camera coupled to the optical delivery system and configured to obtain images of the eye; and an imaging system configured to measure structures of anatomical components of the eye; a processor coupled to the laser source, the optical delivery system, the camera and the imaging system, the processor comprising a non-transitory computer readable medium storing computer executable instructions configured to instruct the processor to perform a process which includes: obtaining an undocked iris image of the eye, the undocked iris image having been taken when the eye is not mechanically coupled to any patient interface device; obtaining a measured astigmatism axis orientation of the eye, the measured astigmatism axis orientation having been measured when the eye is not mechanically coupled to any patient interface device; controlling the camera to take a docked iris image of the eye when the eye is mechanically coupled to a patient interface device; computing a rotation angle of the eye between the docked and undocked iris images, including: defining a parameterized transformation which maps pixel positions in a first iris image, which is one of the undocked and docked iris images, to corresponding mapped pixel positions in a second iris image, which is the other one of the undocked and docked iris images, wherein the parameterized transformation includes a translation mapping using translation parameters, a dilation mapping using a pupil dilation parameter, and a rotation mapping using a rotation angle parameter, wherein the dilation mapping maps a distance between a pixel and a pupil center to a mapped distance based on the dilation parameter while mapping a limbus radius of a limbus of the eye to the limbus radius itself; and optimizing the transformation by minimizing an error term that represents a difference between pixel values of the first iris image at its pixel positions and pixel values of the second iris image at the corresponding mapped pixel positions, to obtain optimized values of the transformation parameters including an optimized rotation angle; and computing a rotated astigmatism axis orientation by rotating the measured astigmatism axis orientation by the optimized rotation angle in a predetermined direction; and while the eye is mechanically coupled to the patient interface device, controlling the laser source and the optical delivery system based on the rotated astigmatism axis orientation to deliver the pulsed laser beam into the eye to correct astigmatism of the eye.

In another aspect, the present invention provides a method for treating a patient's eye, implemented in a laser ophthalmic surgery system, the method including: obtaining an undocked iris image of the eye, the undocked iris image having been taken when the eye is not mechanically coupled to any patient interface device; obtaining a measured astigmatism axis orientation of the eye, the measured astigmatism axis orientation having been measured when the eye is not mechanically coupled to any patient interface device; controlling a camera of the laser ophthalmic surgery system to take a docked iris image of the eye when the eye is mechanically coupled to a patient interface device; computing a rotation angle of the eye between the docked and undocked iris images, including: defining a parameterized transformation which maps pixel positions in a first iris image, which is one of the undocked and docked iris images, to corresponding mapped pixel positions in a second iris image, which is the other one of the undocked and docked iris images, wherein the parameterized transformation includes a translation mapping using translation parameters, a dilation mapping using a pupil dilation parameter, and a rotation mapping using a rotation angle parameter, wherein the dilation mapping maps a distance between a pixel and a pupil center to a mapped distance based on the dilation parameter while mapping a limbus radius of a limbus of the eye to the limbus radius itself; and optimizing the transformation by minimizing an error term that represents a difference between pixel values of the first iris image at its pixel positions and pixel values of the second iris image at the corresponding mapped pixel positions, to obtain optimized values of the transformation parameters including an optimized rotation angle; and computing a rotated astigmatism axis orientation by rotating the measured astigmatism axis orientation by the optimized rotation angle in a predetermined direction; and while the eye is mechanically coupled to the patient interface device, controlling a laser source and a optical delivery system of the laser ophthalmic surgery system based on the rotated astigmatism axis orientation to deliver the pulsed laser beam into the eye to correct astigmatism of the eye.

Preferably, the transformation is defined as:

$$\begin{Bmatrix} x_d \\ y_d \end{Bmatrix} = \vec{T}\left(\begin{Bmatrix} x_u \\ y_u \end{Bmatrix}\right)\left(1 + e\left(\frac{L}{R} - 1\right)\right)*$$
$$= \begin{bmatrix} \cos(\theta) & \sin(\theta) \\ -\sin(\theta) & \cos(\theta) \end{bmatrix}$$
$$\left\{\begin{Bmatrix} x_u \\ y_u \end{Bmatrix} - \begin{Bmatrix} x_{center-u} \\ y_{center-u} \end{Bmatrix}\right\} + \begin{Bmatrix} x_{center-d} \\ y_{center-d} \end{Bmatrix}$$

where $x_u$ and $y_u$ are x and y coordinates of a pixel position in the first one of the undocked and docked iris images, $x_d$ and $y_d$ are x and y coordinates of a corresponding transformed pixel position, e is the pupil dilation parameter and $$\left(1 + e\left(\frac{L}{R} - 1\right)\right)$$

is the dilation mapping, θ is the rotation angle parameter, $x_{center-u}$ and $y_{center-u}$ are the translation parameters representing x and y coordinates of a pupil center in the first one of the undocked and docked iris images, $x_{center-d}$ and $y_{center-d}$ are x and y coordinates of the pupil center in the second one of the undocked and docked iris images, L is the limbus radius, and $$R=\sqrt{(x_u-x_{center-u})^2+(y_u-y_{center-u})^2}$$

is a radial position of the pixel in the first one of the undocked and docked iris images with respect to the pupil center.

Preferably, the step of optimizing the transformation is performed using a set of initial parameter values and a gradient Newton-Raphson iterative method.

In another aspect, the present invention provides a computer program product comprising a computer usable non-transitory medium (e.g. memory or storage device) having a computer readable program code embedded therein for controlling a data processing apparatus, the computer readable program code configured to cause the data processing apparatus to execute the above method.

It is to be understood that both the foregoing general description and the following detailed description are exemplary and explanatory and are intended to provide further explanation of the invention as claimed.

DETAILED DESCRIPTION OF PREFERRED EMBODIMENTS

Figure 1:
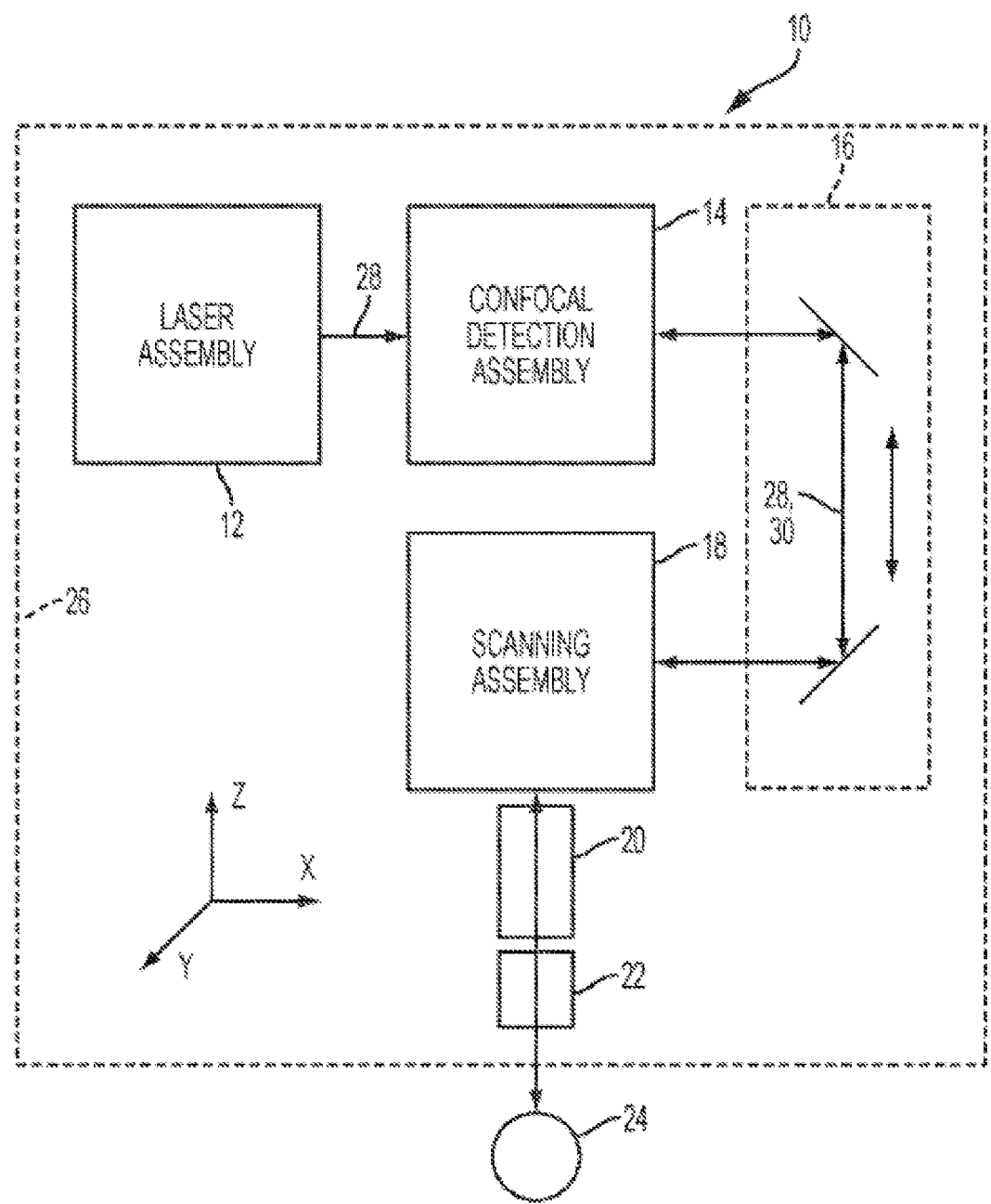
FIG. 1 schematically illustrates an ophthalmic laser surgery system which may be used to implement embodiments of the present invention.

A laser surgery system 10 that may be used to practice embodiments of the present invention is described with reference to FIGS. 1 and 2. As shown in FIG. 1, the laser surgery system 10 may include a laser source/assembly 12, a confocal detection assembly 14, a free-floating mechanism 16, a scanning assembly 18, an objective lens assembly 20, and a patient interface device 22. The patient interface device 22 may be configured to interface with a patient's eye 24. The patient interface device 22 may be supported by the objective lens assembly 20, which may be supported by the scanning assembly 18, which may be supported by the free-floating mechanism 16. The free-floating mechanism 16 may have a portion having a fixed position and orientation relative to the laser assembly 12 and the confocal detection assembly 14. The laser beam 28 may propagate through the free-floating mechanism 16 along a variable optical path 30, which may deliver the beam 28 to the scanning assembly 18. An optical delivery system for receiving and directing the treatment beam may comprise some or all of the components coupled to the to the sub-nanosecond laser assembly 12. In some embodiments, the patient interface device 22 can be configured to be coupled to an eye of the eye 24 using vacuum. The laser surgery system 10 can further optionally include a base assembly 26 that can be fixed in place or be repositionable.

The electromagnetic radiation beam 28 emitted by the laser assembly 12 can include a series of laser pulses of any suitable energy level, duration, and repetition rate. In many embodiments, the laser assembly 12 incorporates sub-nanosecond laser technology where a short duration (e.g., approximately 10 ns to 1 picosecond in duration) laser pulse (with energy level in the tens of micro joules range) can be delivered to a tightly focused point to disrupt tissue, thereby substantially lowering the energy level required to image and/or modify an intraocular target as compared to laser pulses having longer durations. The laser assembly 12 may produce laser pulses having a wavelength suitable to treat and/or image tissue.

The laser assembly 12 may include control and conditioning components. In an embodiment, the control components may include a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. The conditioning components may include an adjustable zoom assembly and a fixed optical relay to transfer the laser pulses over a distance while accommodating laser pulse beam positional and/or directional variability, thereby providing increased tolerance for component variation.

In some embodiments, the scanning assembly 18 can include a Z-scan device and an XY-scan device. The laser surgery system 10 may be configured to focus the electromagnetic radiation beam 28 to a focal point that is scanned in three dimensions. The Z-scan device may be operable to vary the location of the focal point in the direction of propagation of the beam 28. The XY-scan device may be operable to scan the location of the focal point in two dimensions transverse to the direction of propagation of the beam 28. Accordingly, the combination of the Z-scan device and the XY-scan device can be operated to controllably scan the focal point of the beam in three dimensions, including: within a tissue, e.g., eye tissue, of the eye 24. The scanning assembly 18 may be supported by the free-floating mechanism 16, which may accommodate patient movement, induced movement of the scanning assembly 18 relative to the laser assembly 12 and the confocal detection assembly 14 in three dimensions.

Figure 2:
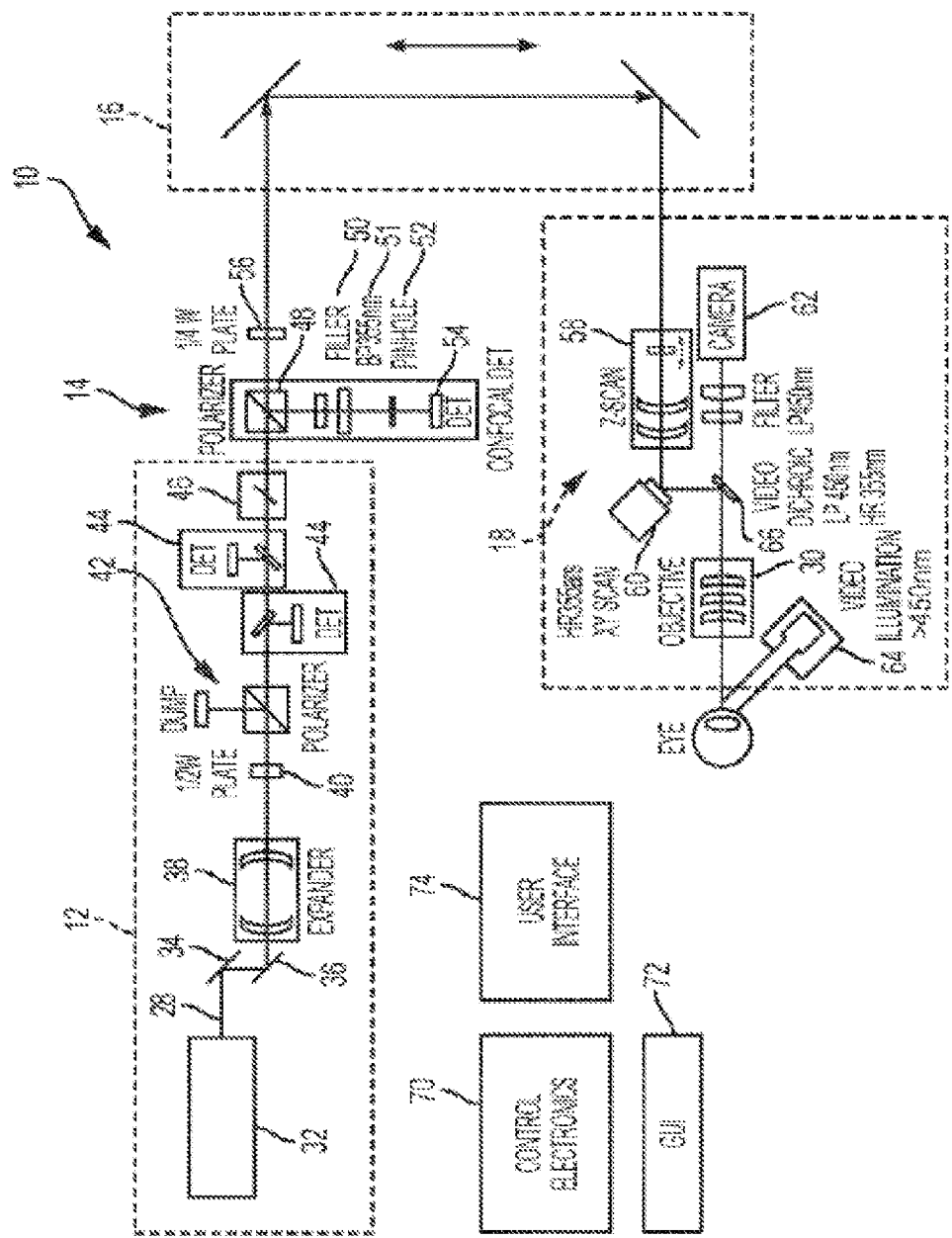
FIG. 2 schematically illustrates an ophthalmic laser surgery system which may be used to implement embodiments of the present invention.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 may include an IR laser 32, alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. The expanded beam 28 may then pass through the one-half wave plate 40 before passing through the polarizer 42. The beam exiting the polarizer 42 may be linearly polarized. The one-half wave plate 40 can rotate this polarization. The amount of light passing through the polarizer 42 depends on the angle of the rotation of the linear polarization. Therefore, the one-half wave plate 40 with the polarizer 42 may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

The system 10 can be set to locate the anterior and posterior surfaces of the lens capsule and cornea and ensure that the laser pulse beam 28 will be focused on the lens capsule and cornea at all points of the desired opening. In the embodiment of FIGS. 1 and 2, a confocal detection assembly 14 is described, although other modalities are within the scope of the present invention. Imaging systems and techniques described herein, such as for example, Optical Coherence Tomography (OCT), Purkinje imaging, Scheimpflug imaging, structured light illumination, confocal backreflectance imaging, fluorescence imaging, ultrasound, or other ophthalmic or medical imaging modalities and/or combinations thereof, may be used to measure structures of the anatomical components of the eye, such as to determine the location and measure the thickness of the lens and lens capsule to provide greater precision to the laser focusing methods. The imaging modalities can perform 2D and 3D patterning. For example, an OCT scan of the eye can provide information about the shape of the cornea, the axial location of the anterior and posterior lens capsule, the boundaries of the cataract nucleus, as well as the depth of the anterior chamber. This information is then loaded into the control electronics 70, and used to program and control the subsequent laser-assisted surgical procedure. The information may also be used to determine a wide variety of parameters related to the procedure such as, for example, the upper and lower axial limits of the focal planes used for modifying the lens capsule, cornea, and synthetic intraocular lens implant, among others.

As shown in the illustrated embodiment, the scanning assembly 18 may include a Z-scan device 58 and an XY-scan device 60. The Z-scan device 58 may be operable to vary a convergence/divergence angle of the beam 28 and thereby change a location of the focal point in the direction of propagation of the beam 28. For example, the Z-scan device 58 may include one or more lenses that are controllably movable in the direction of propagation of the beam 28 to vary a convergence/divergence angle of the beam 28. The XY-scan device 60 may be operable to deflect the beam 28 in two dimensions transverse to the direction of propagation of the beam 28. For example, the XY-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown further in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

The control electronics 70 controls the operation of and can receive input from the laser assembly 12, the confocal detection assembly 14, free-floating mechanism 16, the scanning assembly 18, the objective lens assembly 20, the patient interface 22, control panel/graphical user interface (GUI) 72, and user interface devices 74 via communication paths. The communication paths can be implemented in any suitable configuration, including any suitable shared or dedicated communication paths between the control electronics 70 and the respective system components.

The control electronics 70 can include any suitable components, such as one or more processors, one or more field-programmable gate array (FPGA), and one or more memory storage devices. The control electronics 70 is operatively coupled via the communication paths with the laser assembly 12, the confocal detection assembly 14, the free-floating mechanism 16, the scanning assembly 18, the control panel/GUI 72, and the user interface devices 74. In many embodiments, the control electronics 70 controls the control panel/GUI 72 to provide for pre-procedure planning according to user specified treatment parameters as well as to provide user control over the laser eye surgery procedure. The control electronics 70 can include a processor/controller that is used to perform calculations related to system operation and provide control signals to the various system elements. A computer readable medium can be coupled to the processor in order to store data used by the processor and other system elements. The processor interacts with the other components of the system as described more fully throughout the present specification. In an embodiment, the memory can include a look up table that can be utilized to control one or more components of the laser system surgery system.

The processor can be a general purpose microprocessor configured to execute instructions and data such as a processor manufactured by the Intel Corporation of Santa Clara, Calif. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, combinations thereof, and the like. The memory can be local or distributed as appropriate to the particular application. Memory can include a number of memories including a main random access memory (RAM) for storage of instructions and data during program execution and a read only memory (ROM) in which fixed instructions are stored. Thus, the memory provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

Figure 3:
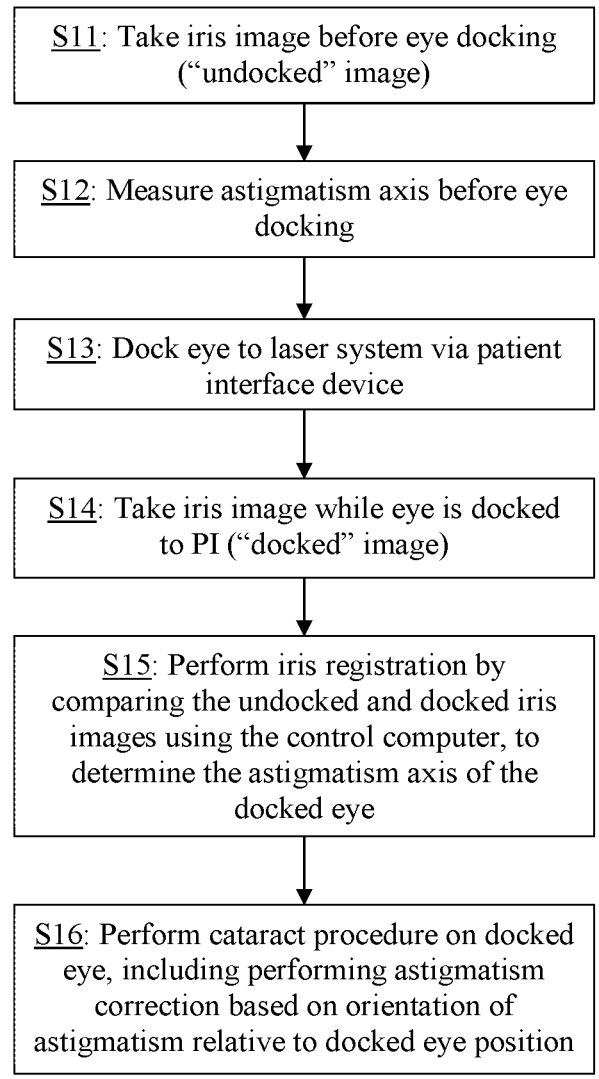
FIG. 3 schematically illustrates an overall procedure of the ophthalmic surgical procedure according to an embodiment of the present invention.

In a laser cataract procedure according to embodiments of the present invention, an iris registration step is performed based on iris images taken before and after the eye is docked to the patient interface (PI) device, as summarized in the flow chart of FIG. 3. First, an iris image is taken while the eye is not docked to the PI (referred to as the "undocked" iris image) (step S11). This may be done, for example using the video camera of the laser system 10. The astigmatism is measured in the undocked condition (step S12), for example, by using the OCT system or other imaging system of the laser system 10. Alternatively, the astigmatism may be measured using a diagnostic system separate from the cataract laser system, in which case the undocked iris image may be taken by the separate diagnostic system as well, and the undocked iris image and the measured astigmatism information are stored in a memory of the control computer of the cataract laser system or another computer system and can be read out during the cataract procedure.

The eye is subsequently docked to the cataract laser system via the PI device (step S13). Another iris image is taken while the eye is docked to the PI (referred to as the "docked" iris image) (step S14). The control computer of the cataract laser system performs an iris registration process (step S15), by first comparing the undocked iris image and the docked iris image to compute a transformation that maps positions in the undocked iris image to positions in the docked iris image, and then applying the transformation to the astigmatism axis of the undocked eye (measured in step S12) to transform it to a rotated orientation relative to the docked iris image, which gives the astigmatism axis of the docked eye. The cataract procedure then proceeds, including the astigmatism correction steps which is performed based on the rotated astigmatism orientation relative to the docket iris image (step S16). The astigmatism correction steps may include forming one or more arcuate incisions on the cornea or sclera, or implanting an IOL having astigmatism correction power; the positions of the arcuate incisions or the orientation of the IOL are dependent on the rotated astigmatism axis orientation.

Figure 4:
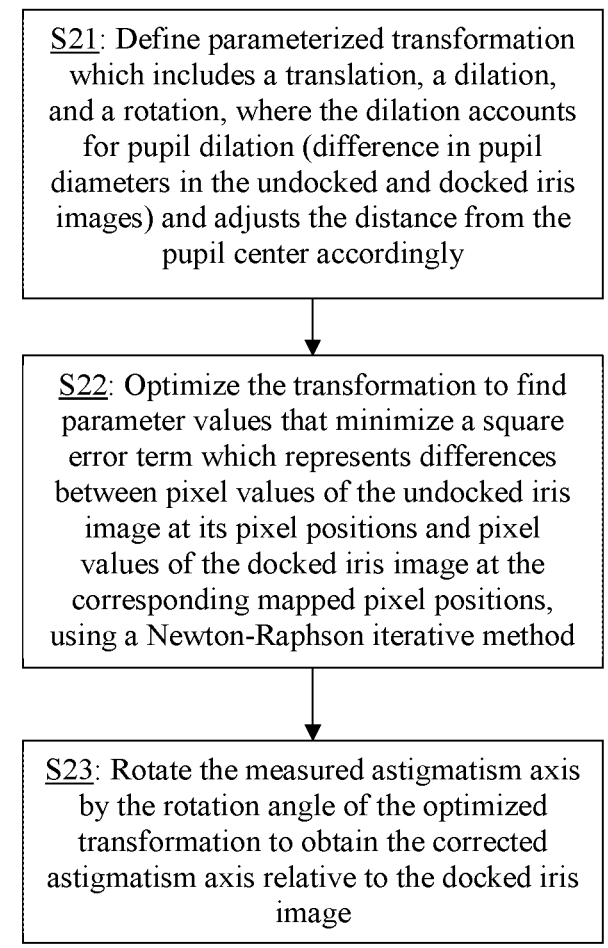
FIG. 4 schematically illustrates an iris registration method according to an embodiment of the present invention.

The iris registration step S15 finds the relative rotation of the eye between the undocked iris image and the docked iris image. To accomplish this, a parameterized transformation is defined, which map pixel positions in the undocked iris image to corresponding mapped pixel positions in the docked iris image; the transformation is optimized such that an error term, which represents differences between pixel values of the undocked iris image at its pixel positions and pixel values of the docked iris image at the corresponding mapped pixel positions, is minimized. This optimization can be thought of as transforming the undocked iris image into a transformed image that overlaps best with the docked iris image. The iris registration algorithm according to an embodiment of the present invention is described with reference to FIG. 4.

First (step S21), a transformation is defined, which includes: a translation mapping, which maps the pupil center in the undocked iris image to the pupil center in the docked iris image; a dilation mapping, which accounts for pupil dilation (difference in pupil diameters in the undocked and docked iris images) and adjusts the pixel distance from the pupil center accordingly; and a rotation mapping, which represents a rotation between the two iris images. The parameters of the transformation that maximize the match between the two iris images are found numerically. The rotation parameter represents the iris rotation angle which can then be used to determine the orientation of astigmatism axis relative to the docked iris image.

More specifically, let $\vec{x}_u$ be a pixel in the undocked iris image, and let its gray level value be $G_u(\vec{x}_u) = G_u(x_u, y_u)$; let $\vec{x}_d$ be a position in the docked iris image that correspond to the pixel $\vec{x}_u$ in the undocked iris image by the transformation $\vec{T}$, i.e., $\vec{x}_d = \vec{T}(\vec{x}_u)$, and let the interpolated pixel gray level value at this position of the docked iris image be $\vec{G_d}(\vec{x_d})=G_d(x_d, y_d)$. The gray level value $G_d(\vec{x_d})$ in the docked iris image is compared with the gray level value $G_u(\vec{x_u})$ of the undocked iris image to find the transformation parameters that maximize the match between them.

In a preferred embodiment, the transformation $\vec{T}$ that maps a pixel position in the undocked iris image to a position in the docked iris image is defined as (Eq. (1)):

$$\vec{x_d} = \begin{Bmatrix} x_d \\ y_d \end{Bmatrix} =$$

$$\begin{Bmatrix} T_x(\vec{x_u}) \\ T_y(\vec{x_u}) \end{Bmatrix} = \vec{T}(\vec{x_u}) = \vec{T}\left(\begin{Bmatrix} x_u \\ y_u \end{Bmatrix}\right) = \left(1 + e\left(\frac{L}{R} - 1\right)\right) * \begin{bmatrix} \cos(\theta) & \sin(\theta) \\ -\sin(\theta) & \cos(\theta) \end{bmatrix}$$

$$\left\{\begin{Bmatrix} x_u \\ y_u \end{Bmatrix} - \begin{Bmatrix} x_{center-u} \\ y_{center-u} \end{Bmatrix}\right\} + \begin{Bmatrix} x_{center-d} \\ y_{center-d} \end{Bmatrix}$$

where e is a pupil dilation parameter, θ is an iris rotation parameter, $x_{center-d}$ and $y_{center-d}$ are the x and y coordinates of the pupil center in the docked iris image, respectively, $x_{center-u}$ and $y_{center-u}$ are the x and y coordinates of the pupil center in the undocked iris image, respectively, L is the limbus radius, and R is the radial position of the pixel $\vec{x_u}$ in the undocked iris image with respect to the pupil center, i.e.

$$R = \sqrt{(x_u - x_{center-u})^2 + (y_u - y_{center-u})^2}$$

The transformation is optimized for the parameters e (dilation), θ (rotation), and $x_{center-d}$ and $y_{center-d}$ (translation), while the parameters $x_{center-u}$, $y_{center-u}$, and L stay constant during the optimization process.

In the transformation $\vec{T}$ defined in Eq. (1), the factor $$\left(1 + e\left(\frac{L}{R} - 1\right)\right)$$

compensates for the effect of pupil dilation (the term dilation is used here to include both dilation and constriction of the pupil); it maps a distance R of a pixel from the iris center to a distance $$\left(1 + e\left(\frac{L}{R} - 1\right)\right).$$

At R=L (i.e. at the radius of the limbus), the mapped distance is unchanged regardless of the value e. In other words, the dilation mapping preserves the limbus location. At R<L (i.e. inside the limbus), the mapped distance is greater than R for e>0 (pupil is dilated) or less than R for e<0 (pupil is constricted). When e=0, mapped distance is unchanged for all distance R. It should be noted that this dilation factor is not an overall scaling of the iris image; rather, it represents the fact that when pupil size changes, the limbus location does not change but the positions of the iris patterns, which are located between the pupil and the limbus, change.

The x and y coordinates of the pupil center of the undocked iris image, $x_{center-u}$, $y_{center-u}$, are computed by fitting the pupil boundary in the undocked iris image to a circle or an ellipse. The limbus radius is computed by fitting the limbus boundary to a circle or an ellipse. If it is fitted to an ellipse, the limbus radius will have two values, one defined along the major axis and one defined along the minor axis. In such a case, the pupil dilation factor can be modified accordingly. Any suitable method may be used to fit the limbus and pupil boundaries. For example, an edge detection algorithm may be used to identify the pupil and limbus boundaries in the images.

Figure 5A:
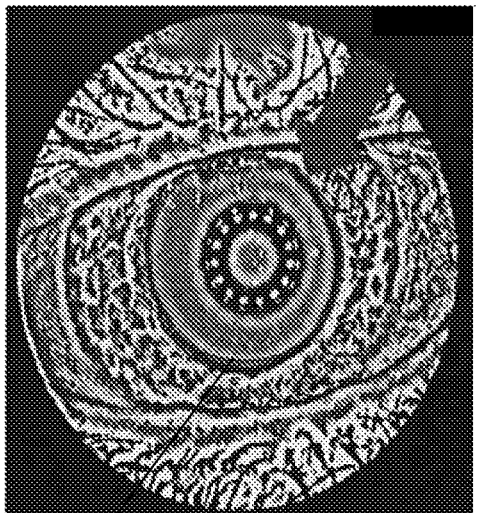
FIGS. 5A-5H are examples that illustrate the effect of various factors in the transformation according to an embodiment of the present invention.
Figure 5B:
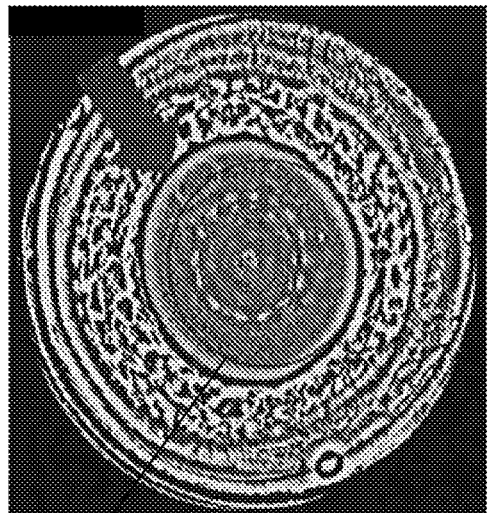
Figure 5C:
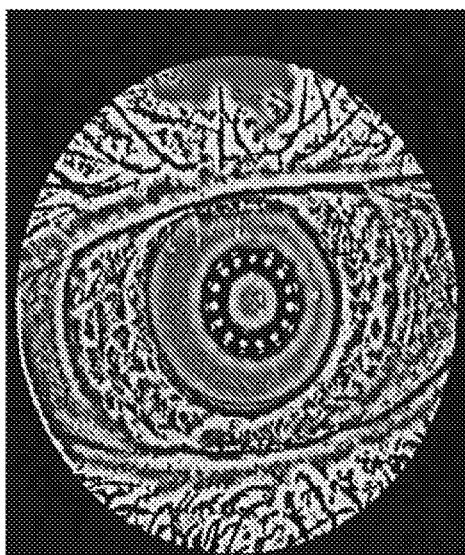
Figure 5D:
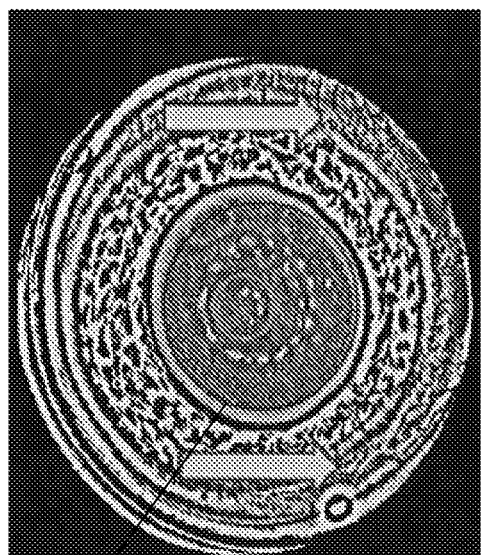
Figure 5E:
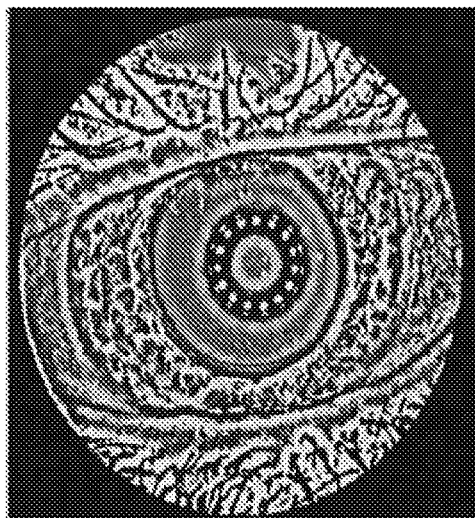
Figure 5F:
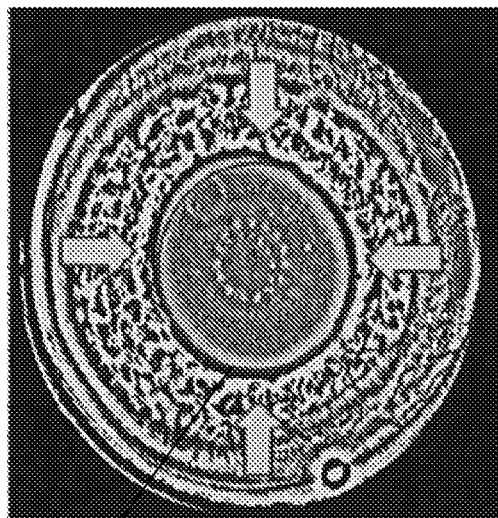
Figure 5G:
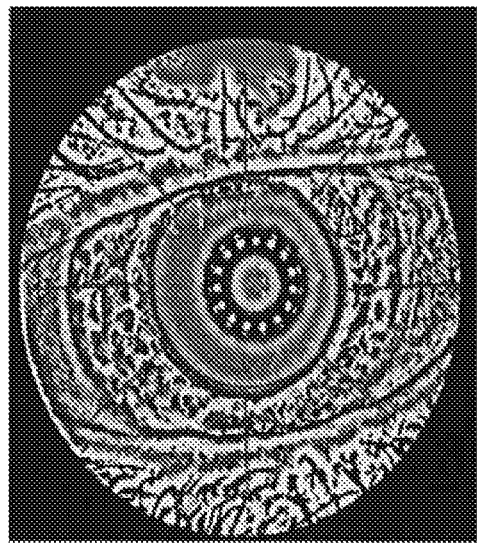
Figure 5H:
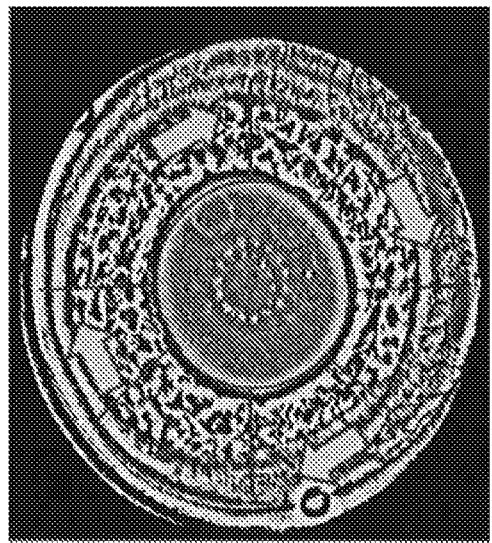

FIGS. 5A-5H are examples that illustrate the effect of the various factors in the transformation. The left ones of the image pairs, namely FIGS. 5A, 5C, 5E, and 5G, are the undocked iris images (they are identical), and the right ones of the image pairs, namely FIGS. 5B, 5D, 5F, and 5H, are docked iris images. In FIGS. 5A and 5B, the dark circles pointed to by the thick arrows are the pupil boundaries. An oval shape 11 is overlaid in the undocked image FIG. 5A that fits the pupil boundary. The oval shape 12 overlaid in the docked image is at the same location as the oval 11 in the undocked image, but it does not coincide with the pupil boundary as the two images are not registered with each other. FIG. 5D shows the effect of translation, where the docked image is translated to the right as indicated by the thick arrows, and the pupil boundary is now more centered with respect to the oval 12. FIG. 5F shows the effect of pupil dilation, where the docked image is applied with the dilation factor as indicated by the thick arrows, and the resulting pupil boundary is now approximately the same size as the oval 12. FIG. 5H shows the effect of rotation, where the docked image is rotated clockwise as indicated by the thick arrows. It should be noted that FIGS. 5A-5H are only intended to aid in understanding of the effect of the transformation factors; in the actual data processing, described in more detail below, the translation, dilation and rotation operations are typically not applied in separate steps in the manner illustrated in FIGS. 5A-5H.

Next (step S22), the transformation is optimized by minimizing an error term. In a preferred embodiment, the optimization of the transformation parameters is done using the Newton-Raphson method to find values of the parameters (θ, e, $x_{center-d}$, $y_{center-d}$) that minimize the square error term $\epsilon$ (Eq. (2)):

$$\epsilon(\theta, e, x_{center-d}, y_{center-d}) = \sum_{i=1}^{pixels} (G_u(\vec{x_{ui}}) - G_d(\vec{x_{di}}))^2 = \sum_{i=1}^{pixels} (G_u(\vec{x_{ui}}) - G_d(\vec{T}(\vec{x_{ui}})))^2$$

The summation here is over all pixels in the undocked iris image within a defined area of interest. In preferred embodiments, the area of interest is the area located between the limbus and a circle interior to the pupil.

The minimization starts with a set of initial parameter values, which may be zero or non-zero. In each iteration of the Newton-Raphson iterative method, first take the gradient of the error term E with respect to each of the four parameters $P_j$, j=1, ... 4 ($P_1=\theta$, $P_2=e$, $P_3=x_{center-d}$, $P_4=y_{center-d}$) at the current parameter values, and express the gradient in a component notation (Eq. (3)):

$$(\nabla \epsilon_{\vec{p}})_j =$$

$$-2 \sum_{i=1}^{pixels} \left[ (G_u(\vec{x_{ui}}) - G_d(\vec{x_{di}})) \left( \frac{\partial G_d(\vec{x_{di}})}{\partial x} \frac{\partial T_x(\vec{x_u})}{\partial P_j} + \frac{\partial G_d(\vec{x_{di}})}{\partial y} \frac{\partial T_y(\vec{x_u})}{\partial P_j} \right) \right]$$

Then take the gradient again with respect to each the four parameters $P_k$, k=1, ... 4 at the current parameter values to construct the Hessian matrix (Eq. (4)):

$$(\nabla\nabla\epsilon_{\vec{p}})_{jk} = -2\sum_{i=1}^{pixels}\left[\left(\frac{\partial G_d(\vec{x_{d_i}})}{\partial x}\frac{\partial T_x(\vec{x_u})}{\partial P_k} + \frac{\partial G_d(\vec{x_{d_i}})}{\partial y}\frac{\partial T_y(\vec{x_u})}{\partial P_k}\right)\right.$$
$$\left.\left(\frac{\partial G_d(\vec{x_{d_i}})}{\partial x}\frac{\partial T_x(\vec{x_u})}{\partial P_j} + \frac{\partial G_d(\vec{x_{d_i}})}{\partial y}\frac{\partial T_y(\vec{x_u})}{\partial P_j}\right)\right]$$

According to the Newton-Raphson iterative process, the gradient of the error term, $\nabla\epsilon_{p_j}$, is expanded in a Taylor series and set equal to zero for a minimum error term (Eq. (5)):

$$0 = (\nabla\epsilon_p)_j = (\nabla\epsilon_p|_{P=P0})_j + (\nabla\nabla\epsilon_p|_{P=P0})_{jk}\{P_{0k} - P_k\}$$

which lead to the equation that gives the updated parameters for an iteration (Eq. (5)):

$$P_k = P_{0k} + (\nabla\nabla\epsilon_p|_{P=P0})_{jk}^{-1}(\nabla\epsilon_p|_{P=P0})_j$$

where $P_{0k}$ are the current parameter values for the current iteration and $P_k$ are the updated parameter values resulting from the current iteration, which will be used in the next iteration. The iterations are repeated until the parameters converge to a set of values that minimizes the square error term $\epsilon$.

Based on the above principle, the minimization process using the gradient Newton-Raphson method include the following steps at each iteration n. First, for every pixel i in the undocked iris image, located at pixel position $\vec{x_{u_i}}$, the corresponding position $\vec{x_{d_i}}$ in the docked iris image is computed using the transformation $\vec{T}$ with the current parameters $P_n$.

Then, the pixel intensity for pixel i in the undocked iris image, $G_u(\vec{x_{u_i}})$, is obtained; the pixel intensity at the corresponding position in the docked iris image, $G_d(\vec{x_{d_i}})$, is computed using an interpolation method. Any suitable interpolation algorithm may be used; one example is a bilinear interpolation using the four nearest pixels. A comparison vector, i.e. the difference between the two pixel intensities, $b_i = G_d(\vec{x_{d_i}}) - G_u(\vec{x_{u_i}})$, is constructed.

Also, for each pixel i, the first derivatives with respect to x and y of the pixel intensity of the docked iris image at the corresponding position $$\vec{x_{d_i}}, \text{ i.e., } \frac{\partial G_d(\vec{x_{d_i}})}{\partial x} \text{ and } \frac{\partial G_d(\vec{x_{d_i}})}{\partial y},$$

are computed, using the interpolation in the previous step.

For each pixel i, the gradients of the transformation $\vec{T}$ in the x and y directions with respect to the parameters $P_j=(\theta, e, x_{center-d}, y_{center-d})$, i.e., $$\left(\frac{\partial T_x(\vec{x_u})}{\partial P_j}\right)_i \text{ and } \left(\frac{\partial T_y(\vec{x_u})}{\partial P_j}\right)_i,$$

j=1, ... 4, are also computed.

Then, the Hessian matrix is computed using the first derivatives and gradients computed above, i.e., $$H_{ij} = \frac{\partial G_d(\vec{x_{d_i}})}{\partial x}\frac{\partial T_x(\vec{x_u})}{\partial P_j} + \frac{\partial G_d(\vec{x_{d_i}})}{\partial y}\frac{\partial T_y(\vec{x_u})}{\partial P_j}$$

Next, the Newton-Raphson system is constructed and solved (where j, k=1, ... 4 are the indices of the parameters):

$$(I^*\lambda + H_{ij}H_{ik})\Delta P_j = H_{ik}b_i$$

In the above Newton-Raphson system, to improve convergence, a damping parameter (Levenberg-Marquardt parameter) $\lambda$ is used. I is the identity matrix.

Finally, the transformation parameters are updated:

$$P_{n+1} = P_n + \Delta P$$

The above steps are repeated for each iteration until the parameter values converge. A predefined threshold may be used to determine convergence.

Once the transformation is optimized, the rotation angle $\theta$ of the transformation is obtained, and the astigmatism axis measured before eye docking is rotated by that rotation angle to obtain the rotated astigmatism axis relative to the docked iris image (step S23).

The convergence radius of the above minimization method can be small, and the process may converge to a local minimum easily but the local minimum may not necessarily be the correct transformation. To overcome this difficulty, in some embodiments, the minimization process is performed several times, each time with a different initial rotation parameter (and optionally, different initial translation and dilation parameters). When all minimizations are completed, if several of them converge to the same rotation angle, with a small error term, this rotation angle will be deemed the correct rotation angle. This redundancy provides assurance that the result is correct.

The minimization process is less sensitive to local minimums when coarsed (lower spatial resolution) images are used. A coarsed image may be generated, for example, by averaging every N by N pixel area of the original (undocked or docked) iris images into a single pixel. The minimization process also runs faster on coarsed images. Therefore, in some embodiments, a coarsed undocked iris image and a coarsed docked iris image may be used in an initial minimization process to find initial conditions, which are then used to perform the minimization process using higher resolution (e.g. the original full resolution) images. In some embodiments, a pyramid method may be used where the minimization process is repeated on progressively higher resolution images (all generated from the original full resolution images), each time using the parameters found in the previous repetition as the initial conditions. Each of the repetitions uses the same minimization algorithm described above but with different images and different initial parameters.

When applying the minimization method to iris images, care should be taken to avoid certain artifacts peculiar to iris images. For example, in a typical undocked iris image, portions of the iris may be covered by the eyelids, whereas in the docked iris image, these portions are visible because the eyelids are kept away by the PI device. Therefore, the two iris images will not match each other in these portions. To address this problem, a preferred embodiment of the present invention includes an outlier adjustment or rejection step. More specifically, in each iteration of the Newton-Raphson minimization process described above, for each pixel in the undocked iris image, the pixel intensity difference between that pixel and the corresponding pixel at the mapped position in the docked iris image is evaluated; pixel pairs that have comparatively greater intensity differences are deemed outliers and assigned comparatively lower weights in the error term $\epsilon$ in the iteration. Any appropriate criteria may be used to determine outliers and to adjust the weights of the pixels. In one embodiment, pixels that have intensity differences greater than a predefined threshold (e.g., a predefined multiplier of the mean intensity difference of all pixels) are assigned a weight of zero (i.e. they are excluded). This method works well to identify eyelids and reduce their deleterious effect on precision and convergence.

As described earlier, in some embodiments, in the undocked iris images, only pixels located between the limbus and the iris/pupil boundary are used in the optimization process. In some embodiments, some pixels inside the pupil are included in the optimization process, which allows for comparison of pupil shapes as well.

It should be noted that since the docked and undocked iris images are symmetrical in their roles, the transformation may be applied to map positions in the docked iris image to positions in the undocked iris image, i.e., $\vec{x}_u = \vec{T}(\vec{x}_d)$, which gives an equivalent result with the calculated rotation angle being a rotation in the opposite direction.

The iris registration method described above may be applied in other laser ophthalmic surgery procedures for astigmatism correction where a patient interface is used to dock the eye, such as small incision lens extraction.

It will be apparent to those skilled in the art that various modification and variations can be made in the iris registration method and related apparatus of the present invention without departing from the spirit or scope of the invention. Thus, it is intended that the present invention cover modifications and variations that come within the scope of the appended claims and their equivalents.

What is claimed is:

1. A laser ophthalmic surgery system for treating a patient's eye, comprising:
   a laser source configured to generate a pulsed laser beam;
   an optical delivery system coupled to the laser source, and configured to receive and direct the pulsed laser beam;
   a camera coupled to the optical delivery system and configured to obtain images of the eye;
   an imaging system configured to measure structures of anatomical components of the eye; and
   a processor coupled to the laser source, the optical delivery system, the camera and the imaging system, the processor comprising a non-transitory computer readable medium storing computer executable instructions configured to instruct the processor to perform a process which includes:
   obtaining an undocked iris image of the eye, the undocked iris image having been taken when the eye is not mechanically coupled to any patient interface device;
   obtaining a measured astigmatism axis orientation of the eye, the measured astigmatism axis orientation having been measured when the eye is not mechanically coupled to any patient interface device;
   controlling the camera to take a docked iris image of the eye when the eye is mechanically coupled to a patient interface device;
   computing a rotation angle of the eye between the docked and undocked iris images, including:
      defining a parameterized transformation which maps pixel positions in a first iris image, which is one of the undocked and docked iris images, to corresponding mapped pixel positions in a second iris image, which is the other one of the undocked and docked iris images, wherein the parameterized transformation includes a translation mapping using translation parameters, a dilation mapping using a pupil dilation parameter, and a rotation mapping using a rotation angle parameter, wherein the dilation mapping maps a distance between a pixel and a pupil center to a mapped distance based on the dilation parameter while mapping a limbus radius of a limbus of the eye to the limbus radius itself; and
      optimizing the transformation by minimizing an error term that represents a difference between pixel values of the first iris image at its pixel positions and pixel values of the second iris image at the corresponding mapped pixel positions, to obtain optimized values of the transformation parameters including an optimized rotation angle;
   computing a rotated astigmatism axis orientation by rotating the measured astigmatism axis orientation by the optimized rotation angle in a predetermined direction; and
   while the eye is mechanically coupled to the patient interface device, controlling the laser source and the optical delivery system based on the rotated astigmatism axis orientation to deliver the pulsed laser beam into the eye to correct astigmatism of the eye.

2. The laser ophthalmic surgery system of claim 1, wherein the transformation is defined as:

$$\left\{ \begin{array}{c} x_d \\ y_d \end{array} \right\} = \vec{T}\left(\left\{ \begin{array}{c} x_u \\ y_u \end{array} \right\}\right) = \left(1 + e\left(\frac{L}{R} - 1\right)\right) * \begin{bmatrix} \cos(\theta) & \sin(\theta) \\ -\sin(\theta) & \cos(\theta) \end{bmatrix} \left\{ \left\{ \begin{array}{c} x_u \\ y_u \end{array} \right\} - \left\{ \begin{array}{c} x_{center-u} \\ y_{center-u} \end{array} \right\} \right\} + \left\{ \begin{array}{c} x_{center-d} \\ y_{center-d} \end{array} \right\}$$

where $x_u$ and $y_u$ are x and y coordinates of a pixel position in the first one of the undocked and docked iris images, $x_d$ and $y_d$ are x and y coordinates of a corresponding transformed pixel position, e is the pupil dilation parameter and $$\left(1 + e\left(\frac{L}{R} - 1\right)\right)$$

is the dilation mapping, $\theta$ is the rotation angle parameter, $x_{center-u}$ and $y_{center-u}$ are the translation parameters representing x and y coordinates of a pupil center in the first one of the undocked and docked iris images, $x_{center-d}$ and $y_{center-d}$ are x and y coordinates of the pupil center in the second one of the undocked and docked iris images, L is the limbus radius, and $$R=\sqrt{(x_u-x_{center-u})^2+(y_u-y_{center-u})^2}$$

is a radial position of the pixel in the first one of the undocked and docked iris images with respect to the pupil center.

3. The laser ophthalmic surgery system of claim 1, wherein the step of optimizing the transformation is performed using a set of initial parameter values and a gradient Newton-Raphson iterative method.

4. The laser ophthalmic surgery system of claim 3, wherein the gradient Newton-Raphson iterative method includes a damping parameter.

5. The laser ophthalmic surgery system of claim 1, wherein the step of optimizing the transformation includes:
    providing a plurality of different sets of initial parameter values;
    performing a gradient Newton-Raphson iterative method a plurality of times, each time using one of the plurality of different sets of initial parameter values, to obtain a plurality of sets of candidate optimized values of the transformation parameters; and
    determining the optimized values of the transformation parameters based on the plurality of sets of candidate optimized values.

6. The laser ophthalmic surgery system of claim 1, wherein the step of optimizing the transformation includes:
    generating a first reduced-resolution iris image from the first iris image, and generating a second reduced-resolution iris image from the second iris image, the first and second reduced-resolution iris images having lower resolution than the first and second iris images, respectively;
    optimizing the transformation by minimizing an error term that represents a difference between pixel values of the first reduced-resolution iris image at its pixel positions and pixel values of the second iris reduced-resolution image at the corresponding mapped pixel positions, to obtain a first set of optimized values of the transformation parameters; and
    using the first set of optimized values of the transformation parameters as initial parameter values, further optimizing the transformation by minimizing an error term that represents a difference between pixel values of the first iris image at its pixel positions and pixel values of the second iris image at the corresponding mapped pixel positions, to obtain a second set of optimized values of the transformation parameters.

7. The laser ophthalmic surgery system of claim 1, wherein the error term is calculated as a sum, over pixels of the first iris image, of a weighted square of a pixel value difference between a pixel value of the first iris image at its pixel position and a pixel value of the second iris image at the corresponding mapped pixel position, wherein a weight assigned to each square of pixel value difference in the sum is determined based on the pixel value difference, wherein the weight is lower for higher pixel value difference, and wherein the weight is zero when the pixel value difference exceeds a predefined threshold.

8. The laser ophthalmic surgery system of claim 1, wherein the error term is calculated as a sum, over pixels within a predefined area of the first iris image, of a weighted square of a pixel value difference between a pixel value of the first iris image at its pixel position and a pixel value of the second iris image at the corresponding mapped pixel position, wherein the predefined area is located between the limbus of the eye and a pupil boundary of the eye, or located between the limbus and a circle within the pupil boundary.

9. The laser ophthalmic surgery system of claim 1, wherein the step of obtaining the undocked iris image of the eye includes the processor controlling the camera to obtain the undocked iris image, and the step of obtaining the measured astigmatism axis orientation of the eye includes the processor controlling the imaging system to measure the astigmatism axis orientation.

10. The laser ophthalmic surgery system of claim 1, wherein the step of obtaining the undocked iris image of the eye includes the processor reading the undocked iris image from a memory of the processor, and the step of obtaining the measured astigmatism axis orientation of the eye includes the processor reading the measured astigmatism axis orientation from a memory of the processor.

11. A method for treating a patient's eye, implemented in a laser ophthalmic surgery system, the method comprising:
    obtaining an undocked iris image of the eye, the undocked iris image having been taken when the eye is not mechanically coupled to any patient interface device;
    obtaining a measured astigmatism axis orientation of the eye, the measured astigmatism axis orientation having been measured when the eye is not mechanically coupled to any patient interface device;
    controlling a camera of the laser ophthalmic surgery system to take a docked iris image of the eye when the eye is mechanically coupled to a patient interface device;
    computing a rotation angle of the eye between the docked and undocked iris images, including:
        defining a parameterized transformation which maps pixel positions in a first iris image, which is one of the undocked and docked iris images, to corresponding mapped pixel positions in a second iris image, which is the other one of the undocked and docked iris images, wherein the parameterized transformation includes a translation mapping using translation parameters, a dilation mapping using a pupil dilation parameter, and a rotation mapping using a rotation angle parameter, wherein the dilation mapping maps a distance between a pixel and a pupil center to a mapped distance based on the dilation parameter while mapping a limbus radius of a limbus of the eye to the limbus radius itself; and
        optimizing the transformation by minimizing an error term that represents a difference between pixel values of the first iris image at its pixel positions and pixel values of the second iris image at the corresponding mapped pixel positions, to obtain optimized values of the transformation parameters including an optimized rotation angle;
    computing a rotated astigmatism axis orientation by rotating the measured astigmatism axis orientation by the optimized rotation angle in a predetermined direction; and
    while the eye is mechanically coupled to the patient interface device, controlling a laser source and an optical delivery system of the laser ophthalmic surgery system based on the rotated astigmatism axis orientation to deliver the pulsed laser beam into the eye to correct astigmatism of the eye.

12. The method of claim 11, wherein the transformation is defined as:

$$\left\{\begin{array}{c}x_d\\y_d\end{array}\right\} = \vec{T}\left(\left\{\begin{array}{c}x_u\\y_u\end{array}\right\}\right) = \left(1+e\left(\frac{L}{R}-1\right)\right)*\left[\begin{array}{cc}\cos(\theta)&\sin(\theta)\\-\sin(\theta)&\cos(\theta)\end{array}\right]\left\{\left\{\begin{array}{c}x_u\\y_u\end{array}\right\}-\left\{\begin{array}{c}x_{center-u}\\y_{center-u}\end{array}\right\}\right\}+\left\{\begin{array}{c}x_{center-d}\\y_{center-d}\end{array}\right\}$$

where $x_u$ and $y_u$ are x and y coordinates of a pixel position in the first one of the undocked and docked iris images, $x_d$ and $y_d$ are x and y coordinates of a corresponding transformed pixel position, e is the pupil dilation parameter and $$\left(1+e\left(\frac{L}{R}-1\right)\right)$$

is the dilation mapping, θ is the rotation angle parameter, $x_{center-u}$ and $y_{center-u}$ are the translation parameters representing x and y coordinates of a pupil center in the first one of the undocked and docked iris images, $x_{center-d}$ and $y_{center-d}$ are x and y coordinates of the pupil center in the second one of the undocked and docked iris images, L is the limbus radius, and $$R=\sqrt{(x_u-x_{center-u})^2+(y_u-y_{center-u})^2}$$

is a radial position of the pixel in the first one of the undocked and docked iris images with respect to the pupil center.

13. The method of claim 11, wherein the step of optimizing the transformation is performed using a set of initial parameter values and a gradient Newton-Raphson iterative method.

14. The method of claim 13, wherein the gradient Newton-Raphson iterative method includes a damping parameter.

15. The method of claim 11, wherein the step of optimizing the transformation includes:
provyding a plurality of different sets of initial parameter values;
performing a gradient Newton-Raphson iterative method a plurality of times, each time using one of the plurality of different sets of initial parameter values, to obtain a plurality of sets of candidate optimized values of the transformation parameters; and
determining the optimized values of the transformation parameters based on the plurality of sets of candidate optimized values.

16. The method of claim 11, wherein the step of optimizing the transformation includes:
generating a first reduced-resolution iris image from the first iris image, and generating a second reduced-resolution iris image from the second iris image, the first and second reduced-resolution iris images having lower resolution than the first and second iris images, respectively;
optimizing the transformation by minimizing an error term that represents a difference between pixel values of the first reduced-resolution iris image at its pixel positions and pixel values of the second iris reduced-resolution image at the corresponding mapped pixel positions, to obtain a first set of optimized values of the transformation parameters; and
using the first set of optimized values of the transformation parameters as initial parameter values, further optimizing the transformation by minimizing an error term that represents a difference between pixel values of the first iris image at its pixel positions and pixel values of the second iris image at the corresponding mapped pixel positions, to obtain a second set of optimized values of the transformation parameters.

17. The method of claim 11, wherein the error term is calculated as a sum, over pixels of the first iris image, of a weighted square of a pixel value difference between a pixel value of the first iris image at its pixel position and a pixel value of the second iris image at the corresponding mapped pixel position, wherein a weight assigned to each square of pixel value difference in the sum is determined based on the pixel value difference, wherein the weight is lower for higher pixel value difference, and wherein the weight is zero when the pixel value difference exceeds a predefined threshold.

18. The method of claim 11, wherein the error term is calculated as a sum, over pixels within a predefined area of the first iris image, of a weighted square of a pixel value difference between a pixel value of the first iris image at its pixel position and a pixel value of the second iris image at the corresponding mapped pixel position, wherein the predefined area is located between the limbus of the eye and a pupil boundary of the eye, or located between the limbus and a circle within the pupil boundary.

19. The method of claim 11, wherein the step of obtaining the undocked iris image of the eye includes using the camera to obtain the undocked iris image, and the step of obtaining the measured astigmatism axis orientation of the eye includes using the imaging system to measure the astigmatism axis orientation.

20. The method of claim 11, wherein the step of obtaining the undocked iris image of the eye includes reading the undocked iris image from a memory, and the step of obtaining the measured astigmatism axis orientation of the eye includes reading the measured astigmatism axis orientation from a memory.

* * * * *